(12) United States Patent
Hobson et al.

(10) Patent No.: US 7,005,549 B2
(45) Date of Patent: Feb. 28, 2006

(54) PERACID PRECURSORS FOR ANTIMICROBIAL USE

(76) Inventors: David W. Hobson, 16307 Deer Crest, San Antonio, TX (US) 78248; Danny O. Helton, 22414 SW. 15th Ave., Newberry, FL (US) 32669

( * ) Notice: Subject to any disclaimer, the term of this patent is extended or adjusted under 35 U.S.C. 154(b) by 222 days.

(21) Appl. No.: 10/752,430

(22) Filed: Jan. 6, 2004

(65) Prior Publication Data

US 2004/0162228 A1  Aug. 19, 2004

Related U.S. Application Data

(60) Provisional application No. 60/438,114, filed on Jan. 6, 2003.

(51) Int. Cl.
*C07C 311/00* (2006.01)
(52) U.S. Cl. .................. 568/30; 564/154; 564/192; 568/31
(58) Field of Classification Search ............... None
See application file for complete search history.

(56) References Cited

U.S. PATENT DOCUMENTS

| | | | | |
|---|---|---|---|---|
| 3,956,396 A | * | 5/1976 | Mageli et al. ............... 568/559 |
| 4,151,106 A | * | 4/1979 | Meenen ....................... 502/160 |
| 4,255,277 A | * | 3/1981 | Smearing .................... 502/160 |
| 4,396,527 A | * | 8/1983 | Matsuyama et al. ... 252/186.23 |
| 4,401,663 A | * | 8/1983 | Buckwalter et al. ........ 514/605 |
| 4,842,765 A | * | 6/1989 | Satomi .................. 252/186.26 |
| 4,917,816 A | * | 4/1990 | Self ...................... 252/186.26 |
| 5,057,479 A | * | 10/1991 | Bock .......................... 502/160 |
| 5,110,495 A | * | 5/1992 | Self ...................... 252/186.26 |
| 5,162,280 A | * | 11/1992 | Bock .......................... 502/160 |
| 5,596,017 A | * | 1/1997 | Otsu et al. ................. 514/517 |
| 5,654,464 A | * | 8/1997 | Abma et al. ................ 558/261 |
| 5,773,459 A | * | 6/1998 | Tang et al. ................. 514/445 |
| 6,174,922 B1 | * | 1/2001 | Arnold et al. .............. 514/604 |
| 6,303,816 B1 | * | 10/2001 | Arnold et al. ................ 564/82 |
| 6,500,865 B1 | * | 12/2002 | Arnold et al. .............. 514/605 |

* cited by examiner

*Primary Examiner*—Gregory R. Del Cotto
(74) *Attorney, Agent, or Firm*—Christopher J. Whewell

(57) ABSTRACT

This disclosure describes unique chemical structures for use as solid or concentrated chemical precursors to the production of peroxy acids when combined with hydrogen peroxide or a hydrogen peroxide precursor such as percarbonates or perborates. Peroxy acids (peracids) such as peroxyacetic acid are used currently to disinfect medical equipment such as endoscopes and related items. It has been discovered that these structures are not currently listed in Chemical Abstracts and do not appear to be the subject of any prior art related to this or any other similar application. The specification for this claim includes chemical structures for each claimed precursor as well as means of synthesis that could be carried our by any skilled synthetic organic chemist. Practical uses for this invention include several antimicrobial applications of which at least one example is included.

1 Claim, No Drawings

PERACID PRECURSORS FOR ANTIMICROBIAL USE

CROSS-REFERENCES TO RELATED APPLICATIONS

This application claims the benefit of U.S. Provisional Application No. 60/438,114 filed Jan. 6, 2003 the entire contents of which are herein incorporated by reference.

BACKGROUND

Subject Matter of Disclosure: Unique chemical structures for use as solid or concentrated chemical precursors to the production of peroxy acids when combined with hydrogen peroxide or a hydrogen peroxide precursor such as percarbonates or perborates. Peroxy acids (peracids) such as peroxyacetic acid are used currently to disinfect medical equipment such as endoscopes and related items. Perpropionic acid or PPA has not been developed for that purpose due at least in part to the lack of an efficient means to produce PPA at the site of use. These precursors can be used to produce novel antimicrobial formulations that are relatively easy to produce and consume less weight of hydrogen peroxide per mole of peracid than the commercial precursors acetyl salicylic acid (ASA) and tetraacetylethylenediamine (TAED). The claimed precursors are more water-soluble than both ASA and TAED. These chemical precursors allow for the formulation of antimicrobial compositions that can be designed to have room temperature stability in its concentrated form and can be alternatively packaged in a dry form for reconstitution with hydrogen peroxide or a hydrogen peroxide precursor with water at the site of application. The resulting liquid formulation can be delivered in liquid or a gaseous form at the site of use. The dry powder form or its concentrate may also be applied to the site of use and activated with hydrogen peroxide or water in combination with a hydrogen peroxide precursor.

Some immediate and anticipated uses for this invention include but are not limited to the following.
1. Emergency disinfection of wounds by mixing dry powder with water
2. Disinfection of medical devices
3. Disinfection of animal enclosure areas such as used by horses, cattle, dogs, cats, etc.
4. Remediation of mold in buildings, the contents of buildings and on plants
5. When used in a volatile form it is useful as a general disinfection such as vegetative bacteria, molds, fungi and their spores for remediation in non-line-of-slight applications
6. In low concentration it can disinfect food items
7. In liquid form as a disinfectant of equipment such as tanks, Jeeps, airplanes and related equipment.

Peracids, peracetic acid in particular, have been used with considerable success with endoscopes and some other environmental surfaces. Peracetic acid at final use concentrations is too unstable to have a significant shelf life. Making a concentrated solution and diluting to final concentration just before usage have addressed the shelf life issue. This approach has the problem of shipping hazardous cargo. Another solution to the shelf life problem is to use a solid formulation and mix with water shortly before needed. The active precursor components would be a solid form of hydrogen peroxide such as percarbonate or perborate plus an acyl donor such as:

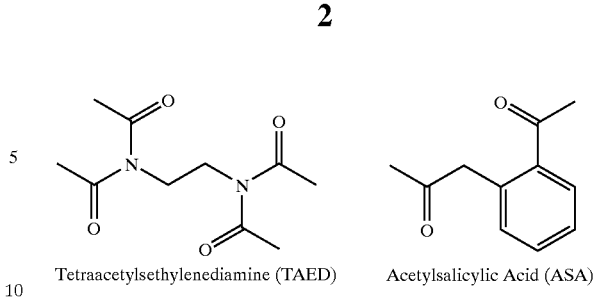

Tetraacetylethylenediamine (TAED)    Acetylsalicylic Acid (ASA)

The molecules TAED and ASA are not efficient acylating agents in that a lot of carbon byproducts are generated. To quickly generate peracetic acid from ASA a reaction temperature above room temperature is required. The present invention uses a peracid precursor that is water soluble at room temperature, and more efficient in generating peracids than commercial precursors TAED and ASA.

In general one can think of the peracid generation process as:

Thus one wants to minimize the molecular weight of L but not make L too reactive, i.e. not so good a leaving group that it reacts with too much with water. For example one would not choose L to be Cl. Practical examples of L include: —NHSO$_3$H and corresponding salts, —NHSO$_2$NH—, and —NHSONH—

These would lead to for example:

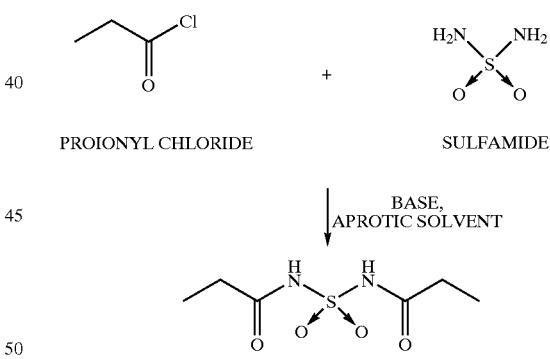

PROIONYL CHLORIDE    SULFAMIDE

BASE, APROTIC SOLVENT

These structures are previously unreported in Chemical Abstracts.

This invention uses a novel water-soluble precursor to generate peracids in a more efficient manner than previously reported. Per mole of peracid generated there are less by-products generated. A smaller weight of novel precursor is required to generate a mole of peracid than with the prior art.

Synthesis of this molecule is well within the means of a skilled practitioner given the instructions for synthesis provided in this disclosure.

The acyl precursors claimed in this invention are more water-soluble than ASA, relatively inexpensive to manufacture and consume less weight per mole of peracid generated than the corresponding ASA.

SUMMARY

The following structures are claimed as novel compounds which can be used as solid precursors to peroxy acids when mixed with hydrogen peroxide or a hydrogen peroxide precursor such as percarbonate or perborate:

R—C(=O)—NH—S(=O)(=O)—NH—C(=O)—R

R=C1 to C20 alkyl or aryl chain or mixed aryl and alkyl chain

R—C(=O)—NH—S(=O)(=O)—NH₂

R=C1 to C20 alkyl or aryl chain or mixed aryl and alkyl chain

R—C(=O)—NH—S(=O)—NH—C(=O)—R

R=C1 to C20 alkyl or aryl chain or mixed aryl and alkyl chain

R—C(=O)—NH—S(=O)—NH₂

R=C1 to C20 alkyl or aryl chain or mixed aryl and alkyl chain

R'—C(=O)—N(R")—S(=O)(=O)—N(R''')—C(=O)—NR''''

R'=C1 to C20 alkyl or aryl chain or mixed aryl and alkyl chain
R"=H or C1 to C20 alkyl or aryl chain or mixed aryl and alkyl chain
R'''=H or C1 to C20 alkyl or aryl chain or mixed aryl and alkyl chain
R''''=C1 to C20 alkyl or aryl chain or mixed aryl and alkyl chain

R'—C(=O)—N(HR")—S(=O)(=O)—NHR'''

R'=C1 to C20 alkyl or aryl chain or mixed aryl and alkyl chain
R"=H or C1 to C20 alkyl or aryl chain or mixed aryl and alkyl chain
R'''=H or C1 to C20 alkyl or aryl chain or mixed aryl and alkyl chain
R''''=C1 to C20 alkyl or aryl chain or mixed aryl and alkyl chain One trained in the art can readily envision variations on the R groups and it is intended that all of these are claimed.

Method of synthesis of novel precursors for peracids: Synthesis of these structures may be described according to the following examples.

EXAMPLE 1

Synthesis of dipropionyl sulfamide—To 100 ml of toluene with stirring add 9.6 grams of sulfamide and 10.1 grams of triethyl amine. Add 9.25 grams of propane chloride drop wise with stirring. Cool as needed to maintain mixture below 60° C. After addition allow mixture to cool to room temperature, filter to remove triethylamine hydrochloride. Evaporate toluene until crystals just begin to form, then cool to 2–8° C. overnight to complete crystallization process. Filter product and dry under vacuum. Store in dessicator.

PROIONYL CHLORIDE    +    SULFAMIDE

↓ toluene/triethyl amine dipropionyl sulfamide

EXAMPLE 2

Same as example 1. except use 13.0 grams of propionic anhydride instead to propionyl chloride.

EXAMPLE 3

Synthesis of dipropionyl sulfoxamide—To 100 ml of toluene with stirring add 8.0 grams of sulfoxamide and 10.1 grams of triethyl amine. Add 9.25 grams of propionyl chloride drop wise with stirring. Cool as needed to maintain mixture below 60° C. After addition allow mixture to cool to room temperature, filter to remove triethylamine hydrochloride. Evaporate toluene until crystals just begin to form, then cool to 2–8° C. overnight to complete crystallization process. Filter product and dry under vacuum. Store in dessicator.

An equivalent molar amount of propionic anhydride may be substituted for propionyl chloride.

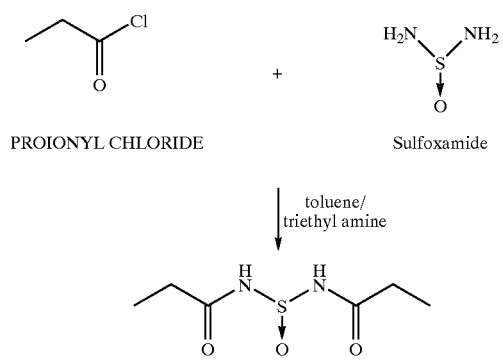

PROIONYL CHLORIDE      Sulfoxamide

EXAMPLE 4

Same as example 3 except use 13.0 grams of propionic anhydride instead of propionic anhydride.

Practical Use Example: Mix an equimolar amount of sodium perborate and dipropionyl sulfamide with water sufficient to generate ~0.4% perpropionic acid. To make one liter of product mix 4.8 grams of dipropionyl sulfamide with 4.65 grams of sodium perborate and add one liter of water. The reaction mixture will be initially basic, then as the reaction proceeds the pH will drop. Sufficient buffer such as sodium dihydrogen phosphate should be added such that the final pH is between ~6.5 and ~7.0. To enhance microbial activity ionic or nonionic surfactants such as dodecylbenzenesulfonic acid or pluronics may be added. Sequestering agents such as ethylenediaminetetraacetic (EDTA) acid may be added to improve microbial activity. As indicated above, many other practical uses for this invention are possible and envisioned.

We claim:

1. Chemical compounds selected from the group consisting of:

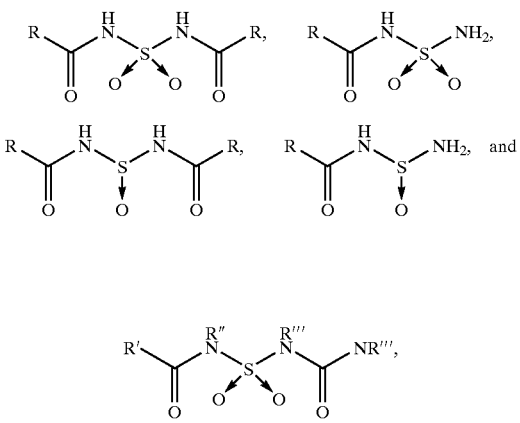

wherein R=C1 to C20 alkyl or aryl chain or mixed aryl and alkyl chain; R'=C1 to C20 alkyl or aryl chain or mixed aryl and alkyl chain; R"=H or C1 to C20 alkyl or aryl chain or mixed aryl and alkyl chain; R'''=H or C1 to C20 alkyl or aryl chain or mixed aryl and alkyl chain; R""=C1 to C20 alkyl or aryl chain or mixed aryl and alkyl chain, said compounds when reacted with a source of peroxide will produce peroxy acids that can be used in various formulations.

* * * * *